US010559383B2

United States Patent
Stewart et al.

(10) Patent No.: US 10,559,383 B2
(45) Date of Patent: Feb. 11, 2020

(54) EMPLOYEE VISIT VERIFICATION SYSTEM

(71) Applicants: Kenneth W. Stewart, Moscow, PA (US); Michael P. Wademan, Nicholson, PA (US); Marilyn S. Major, Elmhurst, PA (US)

(72) Inventors: Kenneth W. Stewart, Moscow, PA (US); Michael P. Wademan, Nicholson, PA (US); Marilyn S. Major, Elmhurst, PA (US)

( * ) Notice: Subject to any disclaimer, the term of this patent is extended or adjusted under 35 U.S.C. 154(b) by 0 days.

(21) Appl. No.: 16/446,600

(22) Filed: Jun. 19, 2019

(65) Prior Publication Data
US 2019/0326009 A1 Oct. 24, 2019

Related U.S. Application Data

(63) Continuation of application No. 16/040,415, filed on Jul. 19, 2018.
(Continued)

(51) Int. Cl.
H04W 4/021 (2018.01)
G16H 40/20 (2018.01)
(Continued)

(52) U.S. Cl.
CPC ........... *G16H 40/20* (2018.01); *G06K 7/1417* (2013.01); *H04W 4/021* (2013.01); *H04W 4/029* (2018.02)

(58) Field of Classification Search
CPC ........... G06K 7/10366; G06K 9/00302; G06K 2009/00939; G06K 7/1417;
(Continued)

(56) References Cited

U.S. PATENT DOCUMENTS 6,591,242 B1 * 7/2003 Karp ...................... G06Q 50/22
705/2
8,019,622 B2 9/2011 Kaboff et al.
(Continued)

FOREIGN PATENT DOCUMENTS

WO 2016/099521 B2 6/2016

OTHER PUBLICATIONS

Sandata website https://www.sandata.com/.
(Continued)

Primary Examiner — Kwasi Karikari
(74) Attorney, Agent, or Firm — Zale Patent Law, Inc.; Atty. Lawrence P. Zale

(57) ABSTRACT

A visitor verification system 1000 is disclosed and described that can automatically authenticate a Mobile Service Provider (MSP) 3 arriving to provide assistance to a patient, or client 5 at their residence 7 while being off-line with the agency server. It also verifies the time and location a MSP session begins, periodically verifies that the MSP 3 is within the client's residence 7, logs the MSP out of the system and reports on the session. The visitor verification system employs at least one visual code located at the residence 7 that is scanned by a mobile computing device (MCD) 100. Information in the visual code is decoded and reconciled with locations determined by executable code (the App) running on the MCD 100. Once the location is verified by the App/MCD 100, the MSP 3 is authenticated. The system includes at least one beacon that transmits a signal that the MSP receives on the MCD 100. The received signal can be used to determine the MSP's distance from the beacon or to monitor the MSP's locations throughout the session. Information acquired during the session may be uploaded immediately, or at a later time when network connectivity is
(Continued)

available, through a network 13 to a server 400 to be used by the system.

16 Claims, 22 Drawing Sheets

Related U.S. Application Data

(60) Provisional application No. 62/535,143, filed on Jul. 20, 2017.

(51) Int. Cl.
*G06K 7/14* (2006.01)
*H04W 4/029* (2018.01)

(58) Field of Classification Search
CPC ............... G06K 9/00087; G06Q 10/06; G06Q 10/1053; G06Q 40/125; G06Q 10/0631; H04W 4/02; H04W 12/08; H04W 12/06; H04W 4/023; H04W 12/00503; H04W 12/00512; H04W 12/02; H04W 4/021; H04W 64/00
See application file for complete search history.

(56) References Cited

U.S. PATENT DOCUMENTS

| | | | |
|---|---|---|---|
| 9,454,751 B1* | 9/2016 | Dickerson | G06Q 10/1091 |
| 9,619,639 B2 | 4/2017 | Donenfeld | |
| 9,697,487 B2 | 7/2017 | Clifford et al. | |
| 2011/0010087 A1* | 1/2011 | Wons | G06Q 10/06 |
| | | | 701/533 |
| 2014/0266604 A1* | 9/2014 | Masood | G06K 9/00221 |
| | | | 340/5.83 |
| 2014/0279672 A1 | 9/2014 | Liu | |
| 2015/0170104 A1* | 6/2015 | Yamada | G06Q 10/1091 |
| | | | 705/32 |
| 2015/0348214 A1 | 12/2015 | Jain | |
| 2016/0132971 A1* | 5/2016 | Teh | G06Q 40/125 |
| | | | 705/32 |
| 2016/0217422 A1 | 7/2016 | Dujisin et al. | |

OTHER PUBLICATIONS

HHAexchange website https://hhaexchange.com/.
MyGeoTracking website https://www.mygeotracking.corn/.
Non-Final Office Action having a Notification Date of May 31, 2019 in parent U.S. Patent Application, U.S. Appl. No. 16/040,415, filed Jul. 19, 2018.
Non-final Office Action dated Aug. 16, 2019 in the parent U.S. Appl. No. 16/040,415, filed Jul. 19, 2018.

\* cited by examiner

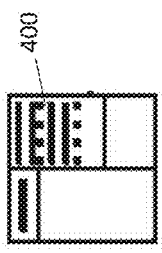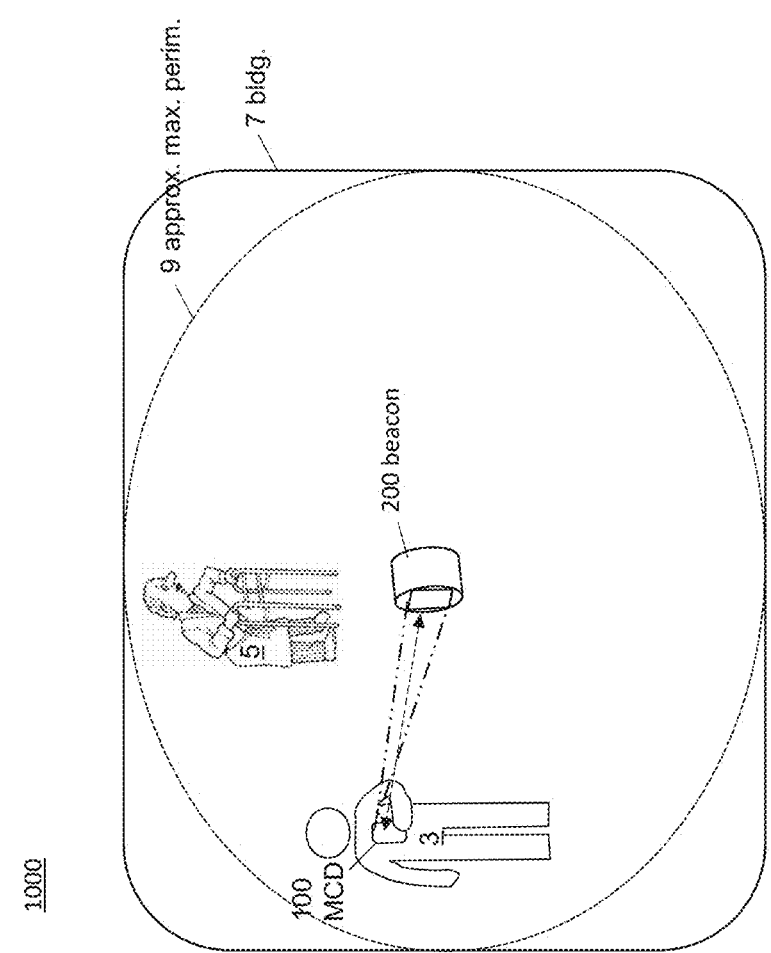
Figure 1

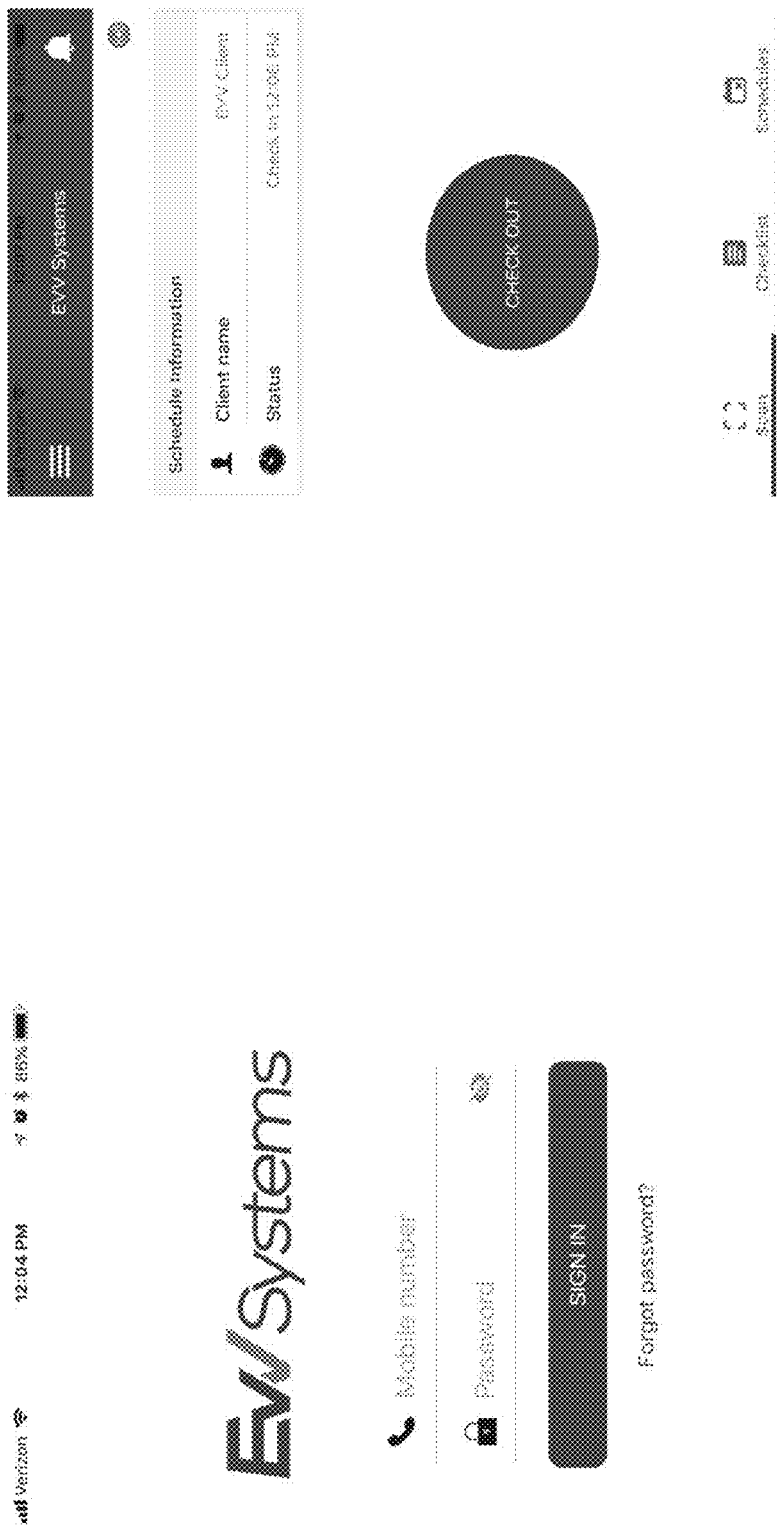

| DATE | TIME | UNIT STATUS | RSSI VALUE | LATITUDE (optional) | LONGITUDE (optional) | MOBILE BATTERY | MOBILE LOCATION | STATUS |
|---|---|---|---|---|---|---|---|---|
| 6/10/2018 | 05:18 PM | | -49 | 41.516423 | -75.674288 | 77% | On | Check Out |
| 6/10/2018 | 05:10 PM | | -81 | 41.51652 | -75.674585 | | On | Range of Motion |
| 6/10/2018 | 05:10 PM | | -81 | 41.51652 | -75.674585 | | On | Wash Dishes |
| 6/10/2018 | 05:10 PM | | -81 | 41.51652 | -75.674585 | | On | Clean Kitchen |
| 6/10/2018 | 05:10 PM | | -81 | 41.51652 | -75.674585 | | On | Clean Bathroom |
| 6/10/2018 | 05:10 PM | | -81 | 41.51652 | -75.674585 | | On | Make/Change Bed |
| 6/10/2018 | 05:10 PM | | -81 | 41.51652 | -75.674585 | | On | BM (Record) |
| 6/10/2018 | 05:09 PM | | -81 | 41.51652 | -75.674585 | | On | Took Medication |
| 6/10/2018 | 05:09 PM | | -81 | 41.51652 | -75.674585 | | On | Lunch |
| 6/10/2018 | 05:09 PM | | -81 | 41.51652 | -75.674585 | | On | Dinner |

Figure 23

EMPLOYEE VISIT VERIFICATION SYSTEM

CROSS-REFERENCE TO RELATED APPLICATIONS

This patent application is a continuation of U.S. patent application Ser. No. 16/040,415, titled "EMPLOYEE VISIT VERIFICATION SYSTEM" filed on Jul. 19, 2018 by Stewart et al. which claims priority to U.S. Provisional Patent application 62/535,143 titled "EMPLOYEE VISIT VERIFICATION SYSTEM" filed on Jul. 20, 2017 by Stewart et al. both of which are hereby incorporated by reference as if set forth in their entirety herein to the extent that they do not conflict with this current disclosure.

STATEMENT REGARDING FEDERALLY SPONSORED RESEARCH

Not Applicable.

BACKGROUND

1. Field of Invention

The present invention relates to a system for verifying when a person visits a specified location, and more particularly a system for verifying when a person visits a specified location and monitoring their visit.

2. Description of Related Art

Sometimes it is necessary to have remote workers, Mobile Service Providers (MSPs), provide services at specific remote locations. One such situation would be when older individuals, physically handicapped individuals and mentally handicapped individuals (collectively referred to as "patients", or "clients") need assistance during the normal course of their day. Home assistance provider companies send MSPs to the residences of these clients to assist them. Some of these services are paid by Medicaid, Medicare and insurance companies. This need also exists for other services provided to clients at their residence, such as at-home assistance or healthcare services.

Unfortunately, some MSPs do not actually provide the assistance they are intended to provide, thereby defrauding the system. One method of defrauding the system is for the MSP to check into a residence, leave for the day and then return later to check out of the system. The current system used to check in and check out is to call a base from the telephone at the residence of the patient.

Now, there is technology available to make calls but make it appear that the calls are originating from a different phone number. More importantly as in-home land lines are replaced with Voice over IP (VOP) and or mobile devices, MSP fraud continues to increase as proper verification devices decreases.

People have also defrauded the system by making check-in calls impersonating the MSP.

Currently, there is a need for an automatic system that accurately authenticates a MSP, and verifies that the MSP actually arrived at the residence, did so at the proper time, stayed for the proper time period, and provided the services being charged.

SUMMARY OF THE INVENTION

The invention may be described as a visit verification (VV) system for verifying visits by a Mobile Service Provider (MSP) to a residence of a client is described that includes a beacon having a transmitter adapted to transmit a signal, a visual code, and a mobile computing device (MCD). The MCD having an optical device adapted to read the visual code on the beacon, a receiver capable of receiving the signal from the beacon, a controller adapted to determine the distance from the beacon based upon the received signal, a communication device adapted to communicate information from the MCD and a server. The server having a network adapter adapted to receive information from the MCD, a memory adapted to store information an input/output (I/O) device adapted to provide output to, and receive input from a user, a controller connected to the network adapter, the memory, and the I/O device. The controller is adapted to authenticate a MSP, determine when the MSP is outside of an acceptable perimeter, and store task status information from the MCD.

The current invention may also be described as a visit verification (VV) system for verifying visits by a Mobile Service Provider (MSP) to a residence of a client having a beacon with an RF transmitter adapted to transmit an RF signal, a visual code, and a mobile computing device (MCD). The MCD having an optical device adapted to read the visual code on the beacon, a receiver capable of receiving the signal from the beacon, a controller running executable code adapted to determine if the visual code matches a prestored code indicating that this is the proper beacon and the distance from the beacon to the MCD based upon the received signal, a direct communication link adapted to communicate information from the MCD to another local computing device. It also includes a server, being a computing device, adapted to receive information periodically from the MCD relating to at least one of login information, RSSI, distance from beacon, longitude, latitude, tasks completed, task status through a manual, direct connection, store and provide information being at least one of a task schedule, clients 3 to visit, beacon UUIDs, addresses, residence locations to the MCD.

The current invention may also be described as a method of verifying visits by a Mobile Service Providers (MSPs) to a residence of a client, comprising the steps of:

providing a schedule of tasks for a Mobile Service Provider (MSP) to perform on a client at client's residence at specific times to a mobile computing device (MCD) of MSP;

the MSP operating executable code on MCD to log into the executable code;

scanning a visual code on a beacon mounted at the residence;

transmitting the visual code to a remote server;

at the remote server, identifying that the visual code relates to the proper residence, the proper client and the proper date/time;

monitoring an RF signal from the RF transmitter;

sending, from the MCD to the server, information indicating distance from the RF transmitter to the MCD;

monitoring the received distance information at the server;

identifying when the distance information exceeds a predetermined maximum, possibly indicating an issue; and receiving at the server status information on tasks being completed from the MCD.

The system may also be described as a visit verification (VV) system that employs at least two verification systems from the group of an RSSI monitoring system which measures and reports a distance from an MCD and a beacon at a fixed location; a visual pattern recognition system which allows the MCD to read a visual pattern, send it to a server, then verify at the server if the visual pattern is the same as the one known to the server; a location device in the MCD that determines its GPS location, communicates this location to the server and determines at the server if the location matches a predetermined location that the MCD should be at a given time and date; a cellular telephone system that can track a location of the MCD and comparing the tracked location to a location known to the server at which the MCD should be at the time and date that it was tracked; an interactive voice response (IVR) system which allows the MSP to use a landline phone to check-in to, and communicate with the server using pushbutton responses and voice recognition; and a digital signature device that allows for the client to sign a digital screen as verification that the MSP has provided services at the client's location.

BRIEF DESCRIPTION OF THE DRAWINGS

The advantages of the system described in this application will become more apparent when read with the exemplary embodiment described in the specification and shown in the drawings. Further, in the accompanying drawings and description that follow, like parts are indicated throughout the drawings and description with the same reference numerals, respectively. The figures may not be drawn to scale and the proportions of certain parts have been exaggerated for convenience of illustration.

FIG. 1 is a simplified block diagram of one embodiment of a visitor verification system according to the current invention.

FIG. 12 is an exemplary screen shot showing a report for a client indicating the MSPs which visited the client, the date/time and status of each visit.

FIG. 13 is a screen shot showing typical information acquired for a MSP.

FIG. 14 is a screen shot showing typical information acquired for a client (patient).

FIG. 16 is a log-in screen for the App on the MCD.

FIG. 17 shows the screen which is displayed after login.

FIG. 23 shows a report of the locations for one or more MCDs. In at least one embodiment, longitude and latitude are not tracked.

DETAILED DESCRIPTION

Figure 2:
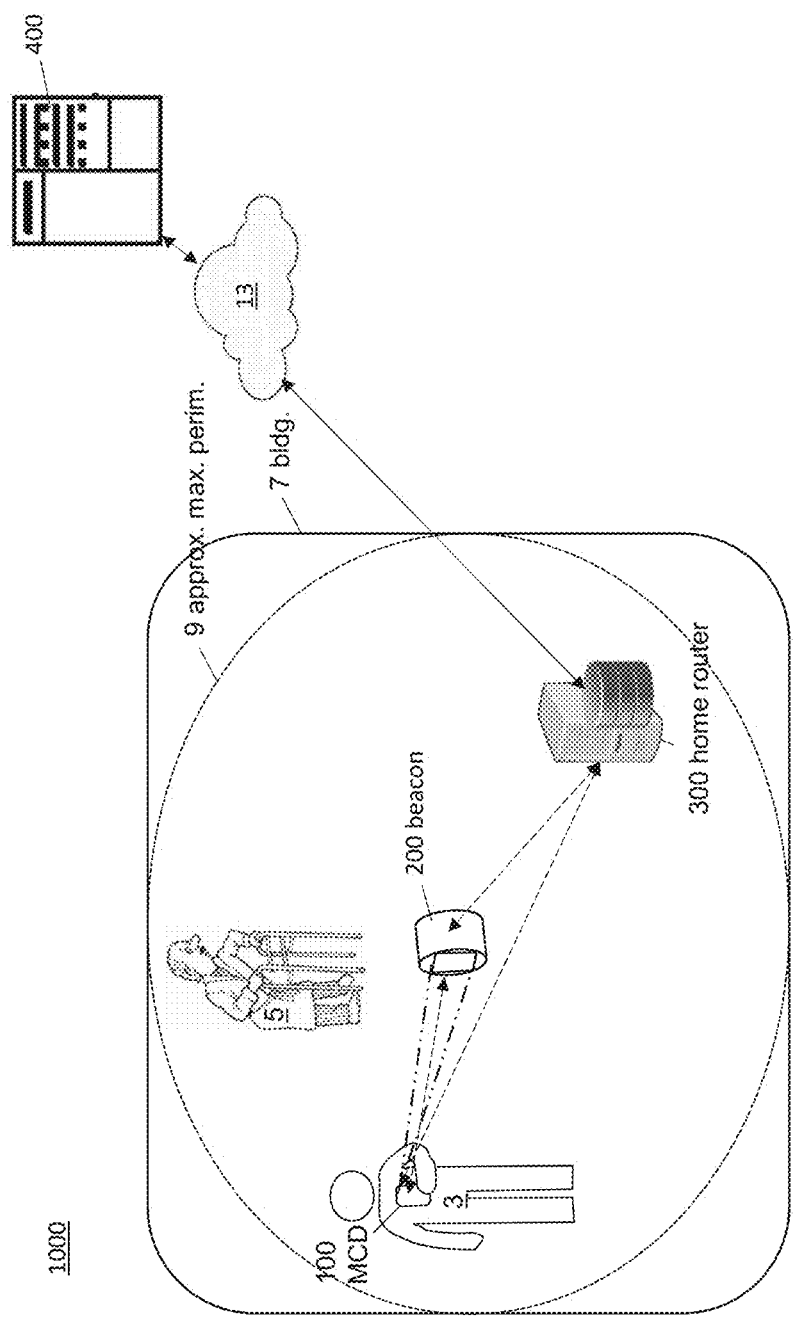
FIG. 2 is a simplified block diagram of another embodiment of a visitor verification system according to the current invention.

The present invention will now be described in detail by describing various illustrative, non-limiting embodiments thereof with reference to the accompanying drawings. The invention may, however, be embodied in many different forms and should not be construed as being limited to the illustrative embodiments set forth herein. Rather, the embodiments are provided so that this disclosure will be thorough and will fully convey the concept of the invention to those skilled in the art. The claims should be consulted to ascertain the true scope of the invention.

1. Theory

As indicated above, there currently are problems with verifying that a MSP actually provides assistance or medical services to a client at their home location. There is the problem of identifying if the proper MSP actually visits the client's location, verifying that the MSP visits at the correct time, verifying that the MSP stays with the client for the designated period of time and that specified services are provided by the MSP to the client during the MSP's visit.

Video surveillance may be used to make the above verifications, but has significant problems. For example, the client's house may have to be wired for the use of cameras. This causes considerable additional costs and become somewhat complex to operate.

The client may not allow setup of this equipment or modification of their residence.

Many of the clients are elderly and may distrust being observed by video cameras.

The use of video cameras to monitor the MSPs reduces their morale and causes them to distrust their employer company.

The system should be less intrusive, require a minimal setup, be accurate and be simple to operate.

The current system is designed to use multiple redundant methods for verification of location, and identity for fraud detection. It employs a beacon fixed at a known location, and monitors the MCDs location relative to the beacon. This ensures that the MCD and MSP are within an acceptable distance from the fixed beacon.

RSSI

It monitors the distance for the beacon using RF signal strength (RSSI) which may be a Bluetooth signal.

Visual Pattern

It also employs a unique visual pattern which must be read within a few feet of the bacon. This may be a screen with a visual code which changes over time. This is sent back to the server which knows the code displayed and compares and verified that the code is correct. This again insures that the MSP is within an acceptable range of the beacon.

MCD GPS

The MCDs have GPS capability and send their GPS location to the base. The server knows the schedule of the MSP indicating where the MSP should be at a given time/date, and can verify if the MSP is in the proper location.

Cellular Phone Network

The MCD may be a cellular telephone. The location of the cellular phone may be determined by the system to indicate the location of the MSP.

IVR

There is an interactive voice response (IVR) system which allows the MSP to use a landline phone to check-in to, and communicate with the server using pushbutton responses and voice recognition when other means of communication are not available.

Digital Signature

The system also allows for the client to sign a digital screen as verification that the MSP has provided services at the client's location.

This system is set up to operate in various locations and conditions. Therefore, it is most accurate when all the above verification methods are functioning. However, it also may function in locations where cellular phone service is not available, relying on other verification means. At least two verification methods may be used to prevent fraud. The additional methods are used to provide greater confidence of the verification.

It can also function in locations which do not have Internet access, again relying on the other verification methods.

In other cases, the battery of the beacon can run down, making the beacon inactive.

The beacon may be moved, or the MCD does not have access to the GPS satellites. In these cases, the other verification means may be used to detect and prevent fraud.

2. Implementation

The current invention may be implemented several different ways.

FIGS. 1-3 and 8 show embodiments of the system in increasing complexity. The embodiment of FIG. 1 illustrates a situation in which a client's residence 7 is remote and does not have radiofrequency connections, such as Wi-Fi, cellular or Bluetooth connections, to public networks 13, such as the Internet.

The embodiments of FIGS. 1-3 and 8 will be described in connection with FIG. 9A.

Figure 9A:
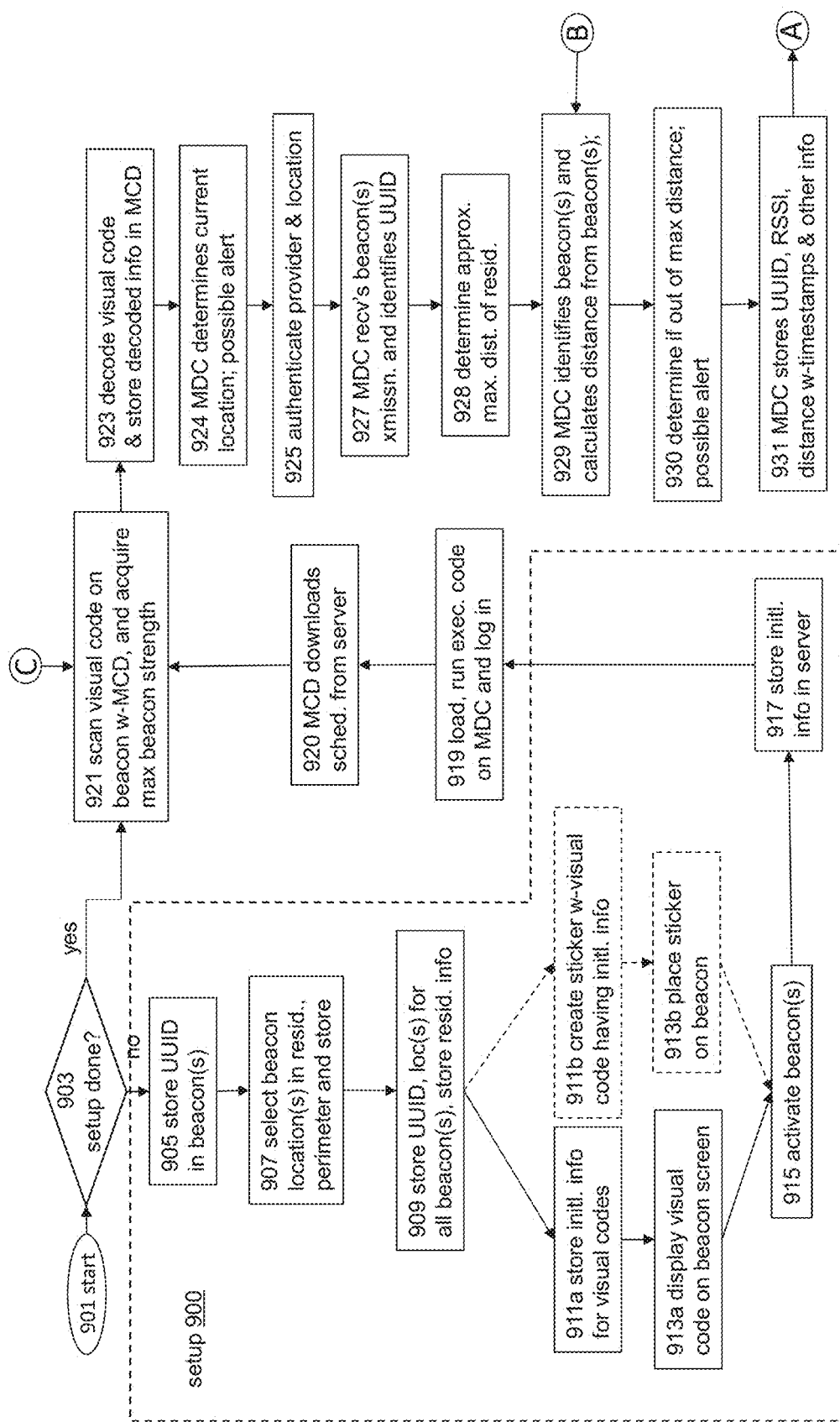
FIGS. 9A, 9B and 9C together are a simplified flowchart indicating the functioning of the systems of FIGS. 1-3 and 8.

The process begins at step 901 in FIG. 9A.

In step 903 it is determined if setup has already been completed. If the setup has already been completed, "yes", then step 919 is performed. If the setup has not already been completed, "no", then setup is performed. Two alternative embodiments of setup are shown as setup 900 being steps 905 through 917

Figure 8:
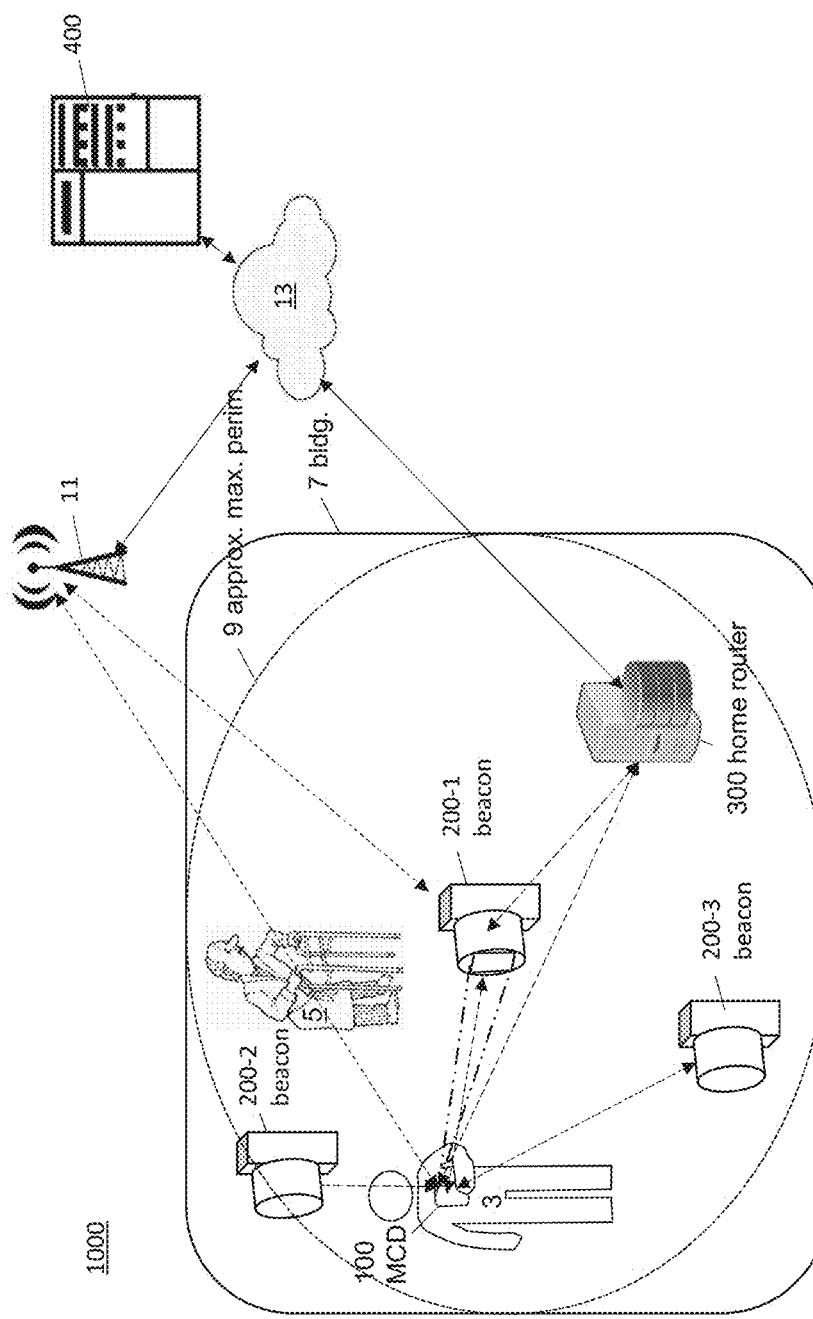
FIG. 8 is a simplified block diagram of another embodiment of a visitor verification system according to the current invention.

In setup 900 of FIG. 9A, in step 905, a Universally Unique Identifier (UUID), or optionally another code used to identify the beacon is incorporated into the beacon 200, or beacons 200-1, 200-2 and 200-3 of FIG. 8. In some cases, these are permanently implemented, similar to a MAC hardware address or a device serial number.

Figure 3:
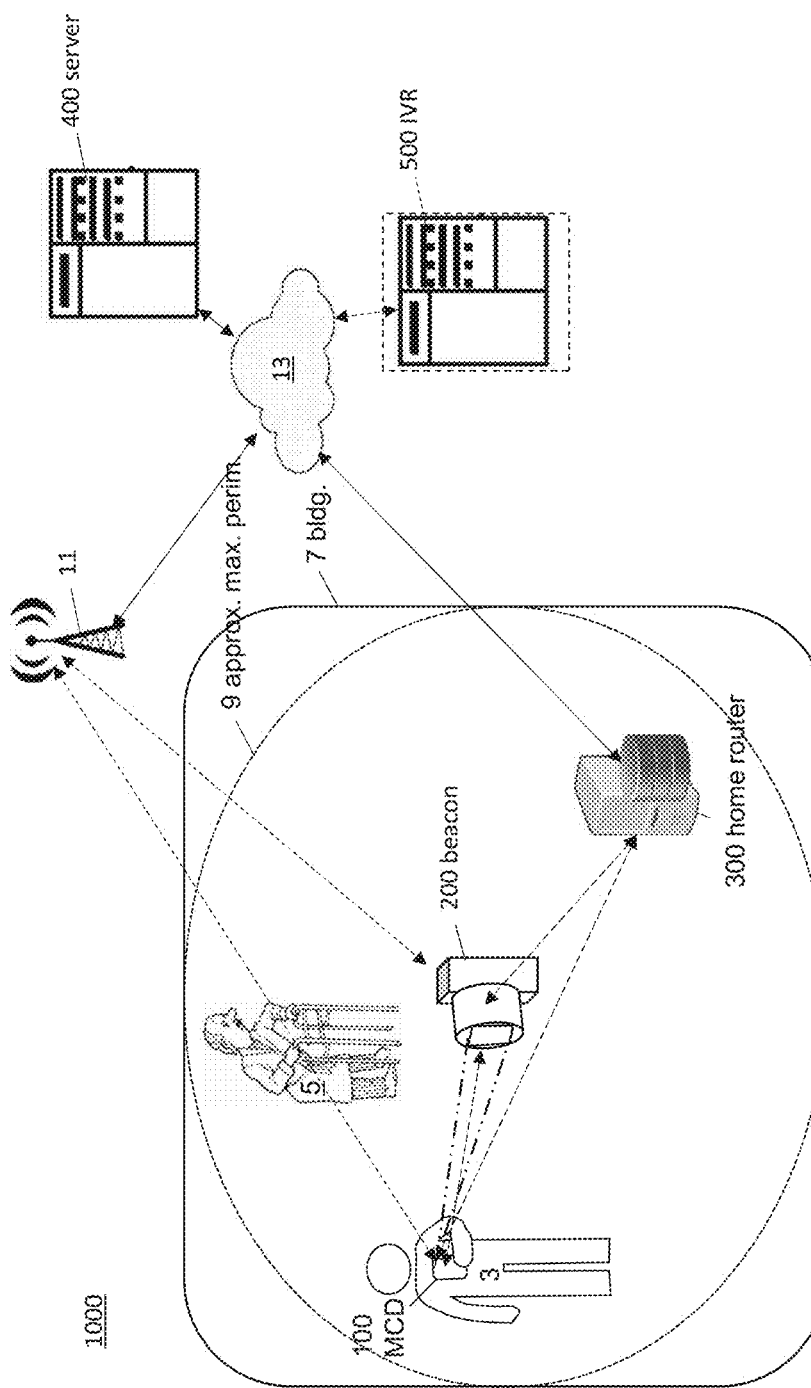
FIG. 3 is a simplified block diagram of another embodiment of a visitor verification system according to the current invention.

In step 907, a location within the residence building of the client that is centrally located relative to the services to be provided is selected for the beacon 200 of FIGS. 1-3.

Multiple beacons 200-1, 200-2, 200-3 of FIG. 8 may be placed separately around the building 7 to allow for triangulation.

In step 909 and in the embodiment in FIG. 1, the UUID and location of the beacon 200 are manually input to a mobile computing device (MCD) 100 carried by MSP 3. This may be copied later to a server 400 when there is a Wi-Fi, cellular or Bluetooth or other connection to the server 400.

Optionally, the location of beacon 200 is also input to the MCD 100.

In the embodiments of FIGS. 2, 3 and 8, the UUIDs and location of the beacon(s) can be provided electronically to the server 400 through a cellular tower 11 in the embodiments of FIGS. 3 and 8. This information may also travel between prestored data 243 through controller 250 and an RF transmitting device 210, (FIG. 5) through an existing home router 300 of residence 7 which connects through a public network, such as the Internet 13 to the server 400. The communication may be through at least one RF transmitting device 210 which may be a Bluetooth communication device 211, or a Wi-Fi device 213.

Home router 300 has a controller 350 connected to a memory 340 which has executable code 341, prestored code and data 343 and a scratch area 345. It also has a communication device 310 with a Bluetooth device 311 capable of communicating with another Bluetooth device, and a wi-fi device 313 capable of communicating with other wi-fi devices.

Figure 7:
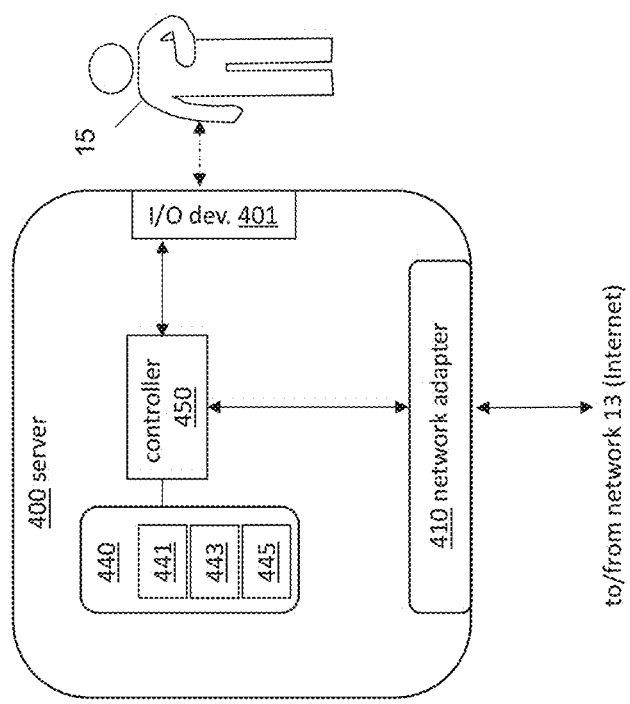
FIG. 7 is a simplified block diagram of an embodiment of a server compatible with the visitor verification systems of FIGS. 1-3 and 8.

Server 400, of FIG. 7, has an input/output device 401 in communication with a controller 450 connected to a memory 440 which has executable code 441, prestored code and data 443 and a scratch area 445. It also has a network adapter 410 capable of communicating with devices on the Internet.

Figure 5:
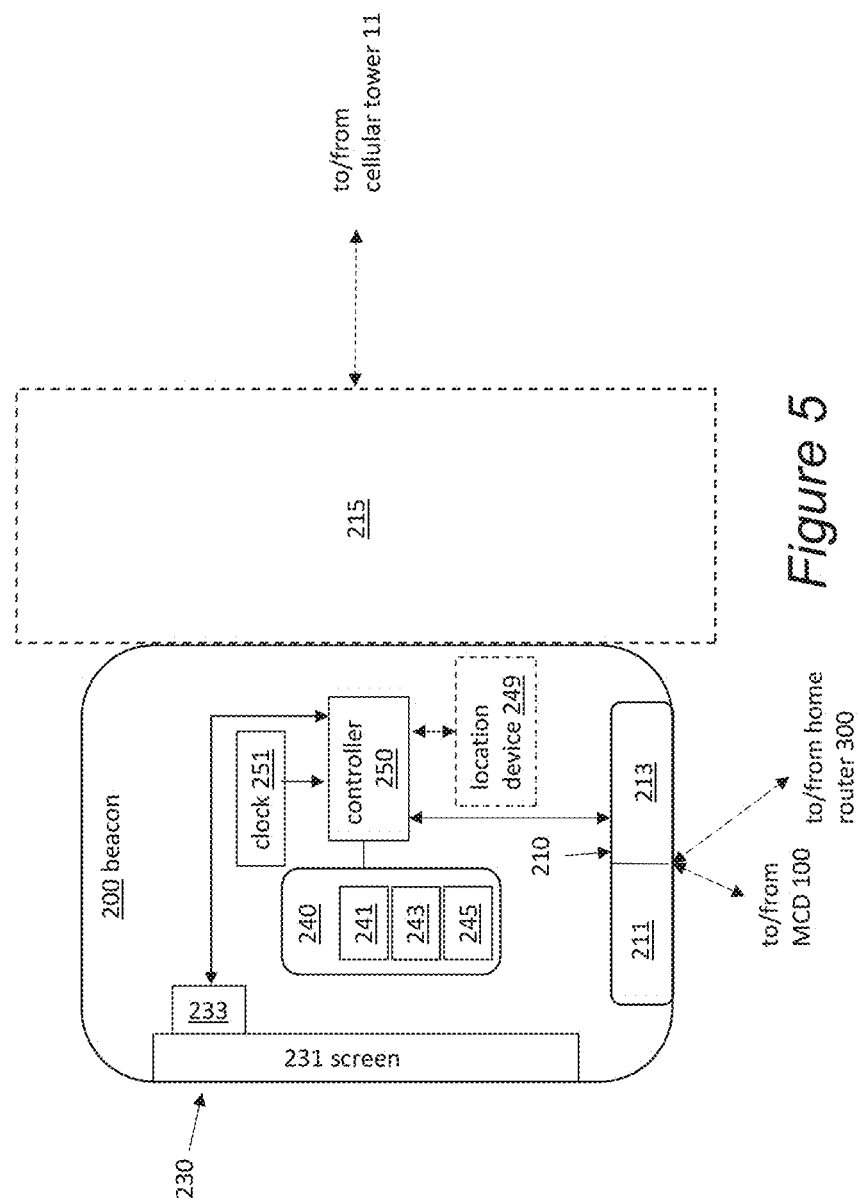
FIG. 5 is a simplified block diagram of an embodiment of beacon having a radiofrequency transmitter, that is compatible with the visitor verification systems of FIGS. 1-3 and 8.
Figure 6:
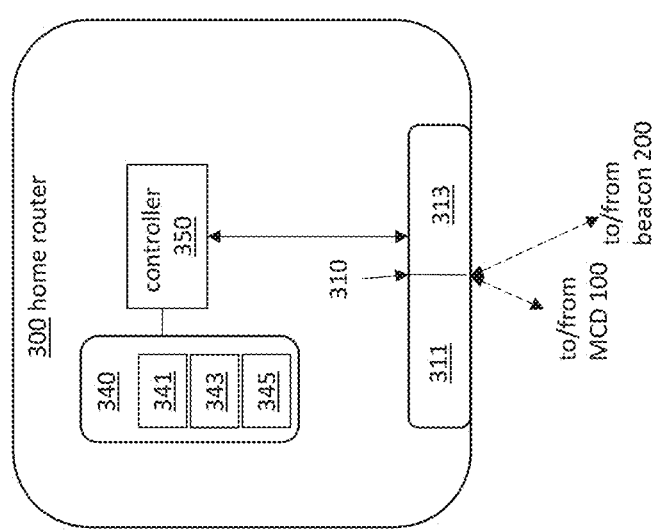
FIG. 6 is a simplified block diagram of an embodiment of a home router compatible with the visitor verification systems of FIGS. 2-3 and 8.

The beacons 200, and at least one of the beacons 200-1, 200-2, 200-3 of FIG. 8 may either have a label with a printed visual code, such as a bar code or QR code, or may include a screen 231 shown in FIG. 5, driven by a video driver 233 and a controller 250 which reads prestored data 243 stored in a memory 240. As with all processors or controllers, they use a scratch area 245 for storing intermediate information used in calculations. This can dynamically produce and display a visual code on screen 231 having information encoded in it.

If the screen 231 and dynamic visual code display is used, then in step 911a information to be displayed on screen 231 is stored in memory 240 of beacon 200 of FIG. 5.

Then in step 913a the visual code is displayed on the screen 231 of beacon(s) 200, or at least one of 200-1, 200-2, 200-3.

If the printed label with the static visual code is being used, then in step 911b a sticker is created having the visual code.

In step 913b, the sticker is placed on the beacon 200, or at least one of 200-1, 200-2, 200-3.

The beacons 200, 200-1, 200-2, 200-3 are activated and begin to transmit RF radiation. It is preferred that they transmit their unique UUIDs in the Bluetooth format.

In step 917, any information which the server 400 requires is either uploaded, for the embodiments of FIGS. 2-3 and 8, or later provided for the embodiment of FIG. 1.

In step 919, executable code 141 required to run hardware of the MCD 100 is downloaded into MCD 100 and run. The MSP 3 logs in and is authenticated at server 400.

In step 920, MCD 100 downloads the current schedule from server 400, if not already downloaded, or to update the schedule.

Optionally, in step 920, if the MSP 3 is in a new residence, the MSP 3 may walk the perimeter of the residence to determine an approximate maximum perimeter of the residence, which is stored.

Setup is now complete and the system begins to run in the operational mode.

A MSP 3 receives an indication that (s)he is to provide either in-home assistance or in-home medical services to a client 5. Client 5 may be a person who is elderly, physically handicapped, or mentally handicapped. This person may need help getting around, dressing, washing, bathing and performing routine tasks. Service companies send MSPs 3 to assist the clients 5 in their residences 7 periodically. The services may be paid, at least in part, by Medicaid, Medicare or insurance companies. The entities require proof that the MSP 3 is the proper person, has arrived in a timely manner to the client's residence 7, and has provided the required services before the entities will pay for the services.

In step 921, the MSP 3 operates the App in MCD 100 to make contact with a server 400. This is done when and where the MCD 100 has network connectivity through a Wi-Fi, Bluetooth, cellular or other connection. The server 400 provides information for the MSP 3 for the day indicating which clients to visit, their residence locations, what time the MSP is to arrive and leave each of the residence locations, the services to provide (tasks to perform), and optionally, the times to perform each service. Other useful information may also be downloaded. Collectively this information is referred to as the "Schedule". In alternative embodiments, the schedule may be downloaded for several days, weeks or other time periods and updated periodically.

After the MSP 3 has downloaded the Schedule, the MSP 3 physically travels to the residence 7 of the client 5.

The MSP 3 may then notify the client 5 that (s)he is to provide services for the client 5. The MSP brings the pre-loaded MCD 100 to the residence 7 and finds the beacon 200.

Figure 4:
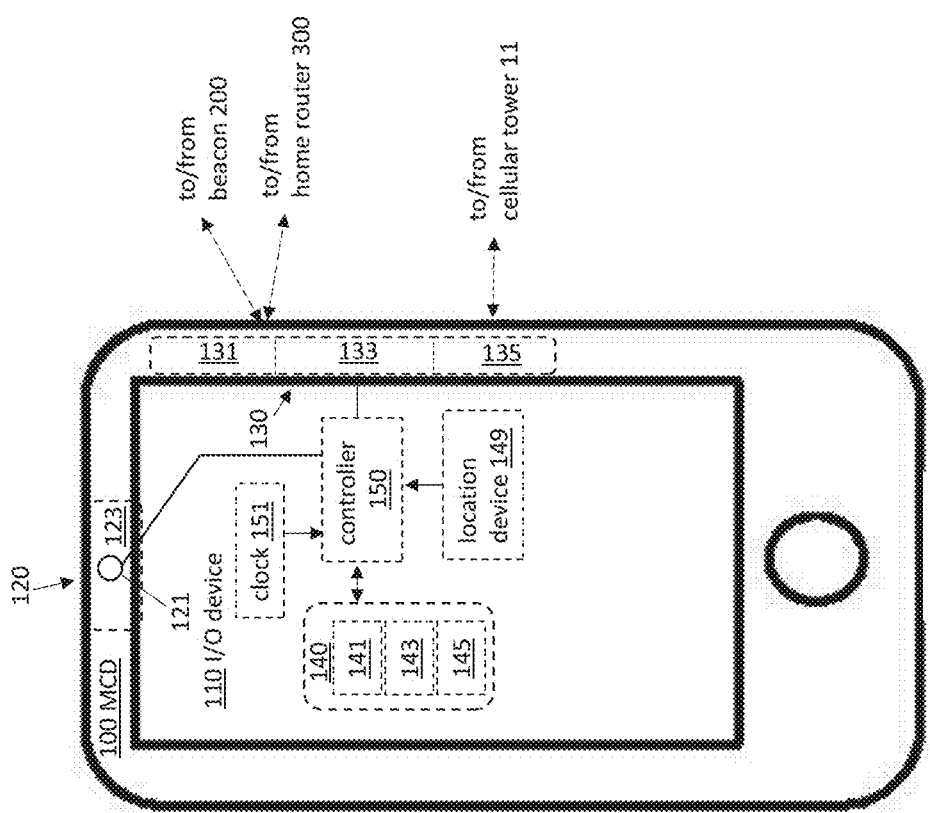
FIG. 4 is a simplified block diagram of an embodiment of a mobile computing device compatible with the visitor verification systems of FIGS. 1-3 and 8.

In step 921, the MSP 3 interacts with the MCD 100 shown in FIG. 4. The MSP 3 interacts with an input/output device 110, which may be a touchscreen. A controller 150 runs executable code 141 (which may include at least one App) stored in storage 140 of MCD 100. The controller 150 may also access prestored data 143 and use the scratch area 145 of MCD 100.

This will allow MSP 3 to select a button on the input/output device to scan the visual code.

The executable code allows MSP 3 to activate a visual decoder 120 which has a camera 121 that scans the visual code on the beacon 200.

Since the MCD 100 is close to the beacon 200, it can also measure and estimate the maximum signal strength of the beacon transmission. Preferably, the transmission of the beacon 200 is Bluetooth transmission; however, it may be any type of electronic transmission which can be received by the MCD 100.

In step 923, a decoder 123 decodes the scanned visual code into fields and values that were encoded in the visual code. This may be the client's name, beacon locations, beacon UUID codes, as well as other information.

MDC 100 has a location device 149, which may be a GPS system, as indicated in FIG. 4.

In step 924, MDC 100 determines a location using location device 149, which may be a GSP device, that can be used to identify if MDC 100 and MSP 3 are near of at least one beacon 200 and residence 7.

Note that the location device 149 can be read when the MCD 100 reads the visual code on beacon 200. At that time, the location device 149 and stored location of the beacon 200 should be close if the MSP 3 is at the proper location.

If the MSP 3 and MDC 100 are not at a residence location specified in the Schedule within a predefined period of time, a notification or alert is sent by the App running on the MDC 100 to the server 400 that the MSP 3 is late for a session. This may also be displayed on the I/O device 110 of MCD 100 as shown in FIG. 4.

In an alternative embodiment, the MCD 100 can determine its current location, check the Schedule to get the location and time of the next session and use existing software to determine the travel time to the location of the next session. It there is not enough time to make it to the session location, a notification or alert is sent to the server 400 and/or presented to the MSP 3 that they will be late for the session.

In step 925, the decoded information, such as the UUID, decoded information from the visual code on the label, or displayed on the screen of the beacon(s) 200, 200-1, 200-2, 200-3, provided by MCD 100 is compared to information in the Schedule by the App to identify the proper MSP 3 is at the proper residence 7 at the right time for check-in. This may be done by comparing the decoded information to information in the MSP's schedule previously uploaded and using an internal clock 151 and an optional location device 249 in the beacon 200 as shown in FIG. 5 may be used to determine the beacon's location which can be used for verification and cross-checking purposes.

In alternative embodiments, the MCD 100 can send GPS coordinates with a MCD ID or equivalent for the MCD hardware, and/or send an ID of the cellular chip to server 400 for further authentication. One such MCD ID code could be a MAC hardware code.

In embodiments of FIGS. 2-3 and 8, the server can send any information or codes that are encoded by the controller 250 of FIG. 5 running executable code 241 in storage 240.

This information is then displayed on screen 231 and read by visual decoder 120 of FIG. 4. MCD 100 then sends this information back through communication device 130 which has at least one of Bluetooth 131, Wi-Fi 133, and/or cellular 135 transceivers. Therefore, the systems of FIGS. 2-3 and 8 can interactively check the identity and location of MSP 3.

In step 927, MDC 100 receives a transmission from beacon 200, and recognizes its UUID.

In step 928, if the MSP 3 is in a new residence, the MSP 3 may walk the perimeter of the residence to determine an approximate maximum perimeter of the residence, which is stored or the program or the program or establishes a GEO fence based upon predefined parameters.

In step 929, MCD 100 then determines the distance of MSP 3 from beacon 200. This may be done by measuring the received signal strength indication (RSSI) of the beacon 200 transmission and comparing it to the maximum signal power of the beacon transmission, measured when the MCD 100 is close to or touching the beacon 200 during check-in. The comparison determines a distance between the MCD 100 and the beacon 200. MCD also creates a timestamp for each measurement using an internal clock (151 of FIG. 4) that are stored with the measurements. Alternatively, these timestamps may be generated by a clock 251 in beacon 200 as shown in FIG. 5.

In step 931 it stores the UUID, calculated distance of the MCD 100 from the beacon 200 with timestamps, along with other information.

In another embodiment, the RSSI is stored. In another embodiment, the actual 2D or 3D location of the MSP 3 are monitored and stored. For privacy reasons, the monitoring is only active when the MSP 3 checks-in and is inactive when the MSP 3 checks out.

Now the current system will be explained in connection with FIGS. 1-3, 8 and 9B.

In step 933, this information is transmitted to the server 400.

Step 935*a* pertains to systems which only have a single beacon 200, such as those shown in FIGS. 1-3. Steps 935*b*, 937*b* and 939*b* pertain to a system having more than one beacon, such as that shown in FIG. 8.

In step 935*a*, the executable code of the App in MCD 100 (or alternatively, the server 400 of the system shown in FIGS. 1-3) compares the distance between the MCD 100 and the beacon 200 to the approximate maximum perimeter of the residence 7 to determine if the MCD 100 and MSP 3 carrying it are within the residence 7.

Optionally, GPS coordinates from the decoded visual code are stored in the MCD 100 and the App compares them to the MCD GPS coordinates to determine if MSP 3 is within an acceptable perimeter (Geo Fence) around the client.

If it is determined that the MCD 100 is outside of an acceptable range, and for at least a specified period of time, then an alarm or notification is sent. This may be send back to server 400, and/or presented to MSP 3. This may be in the form of a visual or audible message.

Optionally, step 937*a* may be performed. The executable code on the MCD 100 interacts with the MSP 3 to allow the MSP to check off tasks as they are performed. A timestamp is created and associated with each completed task. The distance from the beacon 200 is also stored. In alternative embodiments, the longitude and latitude, or the RSSI values may be stored. This information is provided to server 400.

Server 400 can then identify if the MSP 3 was within the residence when MSP 3 indicated that the task was performed. This information is approximate and will be used in conjunction with other information to make determinations and should not be used as the sole determination.

If the automated authentication systems are not able to check-in the MSP, an alternative embodiment may be employed. The embodiment shown in FIG. 3 may also include an interactive voice response (IVR) system 500 that acts as a failsafe feature. IVR system 500 allows the MSP to use telephony to check into a session when the automated authentication is not functioning properly. This may occur when the Schedule downloaded to the MCD 100 does not match that of server 400.

The MCD 100 will display a call button on its I/O 110 that when pressed, take an image of the visual code on beacon 200 and decodes it to dial the IVR.

This connects the MSP 3/MCD 100 to the IVR system 500 through a telephone system.

The App/MCD 100 has already identified the MSP as an employee through the MSP's user ID, (login).

The MCD 100 running the APP decode the visual code to identify the client, and the geo coordinates from the visual code. The APP obtains the geo coordinates from the location device 149 of MCD 100. The APP then compares the MCD geo coordinates against the visual code geo coordinates.

The APP obtains the UUID of the Radio Frequency transmitter in the beacon 200. The APP obtains the RSSI and calculates the distance from the MCD 100 to beacon 200. The distance should be one meter or less for check-in.

The distance monitoring of the MSP 3/MCD 100 from the beacon 200 is performed in the same manner as that described in FIG. 1.

The client's signature may be required at check-out as a further verification that the MSP 3 was present. A notification or alert will be sent to supervisor to sync the Schedule for this MSP on server 400 at some later time.

A check list that is associated with the client will prompt the MSP to confirm that services were provided.

In the system shown in FIG. 8, there are several beacons 200-1, 200-2, 200-3. Each has been preloaded with a unique UUID that is sent in the transmission of each. Also, the location of each beacon is known to the server 400 from the setup phase.

In step 935*b*, the MCD 100 receives the transmissions from beacons 200-1, 200-2 and 200-3 and can identify which signals are coming from which beacons. This is done by identifying the UUID code in each transmission.

Since there are more than one beacon 200-1, 200-2, 200-3, during the setup phase, in one embodiment, the MSP 3 touches or places the MCD 100 against each of the beacons to measure the signal strength at the beacon's surface. This is used to calculate a maximum signal strength of each beacon. The maximum signal strength of each beacon in combination with the received signal strength of each beacon will indicate a distance from that beacon.

In alternative embodiment of the systems of FIGS. 1-3 and 8, the battery voltage may be encoded and sent in beacon transmissions to the MCD 100, or encoded in the visual code displayed on the screen 231 of beacons of FIGS. 2-3 and 8.

In the system of FIG. 8, the received signal strength of each beacon is adjusted by the maximum signal strength of each beacon to determine the distances from beacons 200-1, 200-2, 200-3.

Optionally, step 937*b* may be performed. The executable code 141 in the MCD 100 interacts with the MSP 3 to allow the MSP to check off tasks as they are performed. A timestamp is created and associated with each completed task. The location of MCD 100 is also stored. This information is provided to server 400.

In step 939*b*, in an alternative embodiment, if the server 400 has previously received dimensions, or a perimeter of the residence 7, it can then identify where the MSP 3 is located. Server 400 can also identify when tasks were performed and indicate if tasks were not performed in the specific room or location where the service is commonly provided. For example, if it was identified that the client was dressed, but the calculated location indicates that the MCD 100 was in the kitchen, it would be noted. This information alone will not be used to indicate problems, but will be used in connection with other information to identify problems.

MCD 100 uses the distances from the beacons and the locations of the beacons to triangulate to determine the location of the MCD 100 and MSP 3.

In step 951, it is determined if it is the end of the shift for the MSP 3. If not, ("no") processing continues at step 921 of FIG. 9A.

If so, ("yes") then the MSP begins checkout procedures in step 953.

In step 955, it is determined if the MSP 3 should visit another client's residence 7. If so, ("yes"), then the MSP 3 goes to the location indicated for the next client's residence 7 in step 955. Processing then continues at (C) on FIG. 9A.

If not ("no"), then the MSP 3 logs out of the App on MCD 100 in step 957.

Processing stops at step 961.

Figure 9B:
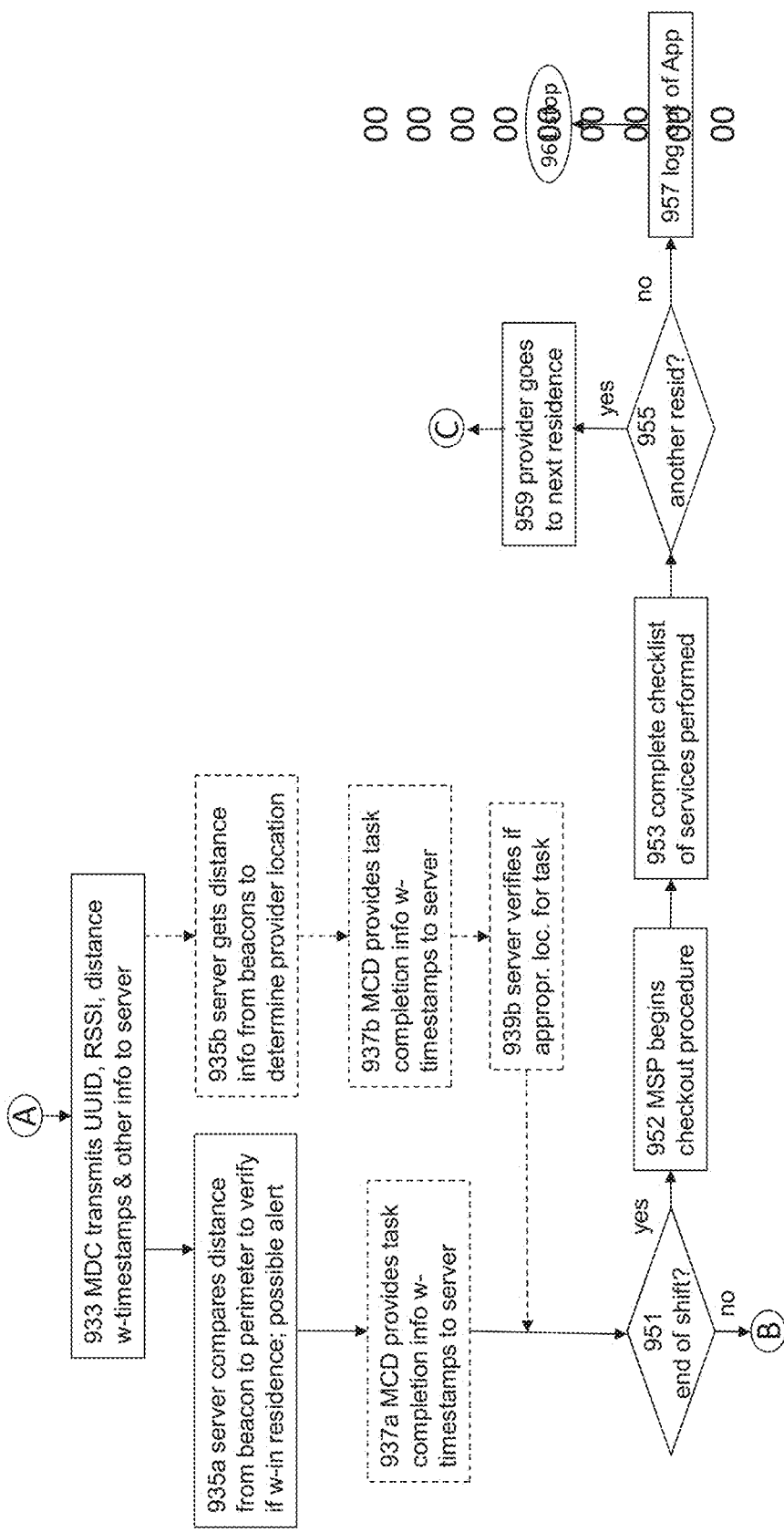
Figure 9C:
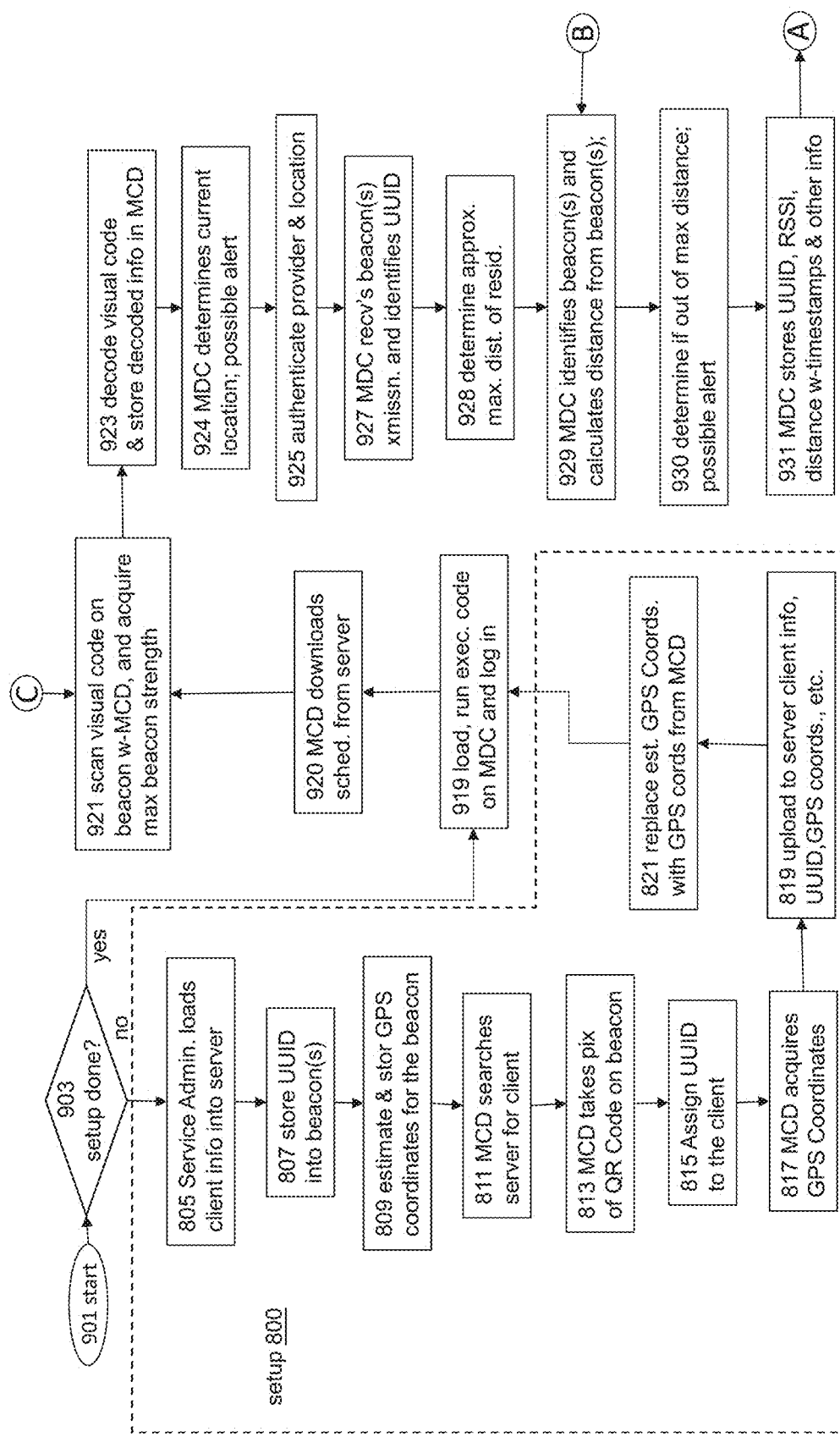

In FIG. 9C, an alternative setup is described. This employs an alternative setup 800 that includes steps 805 through 821. (It is understood that steps 919 through 931, and all steps of FIG. 9B are executed after setup 800.)

The previous embodiment shown in FIG. 9A incorporated setup 900.

In FIG. 9C, the process starts at step 901.

If in step 903, it is determined that setup has not yet been completed ("no"), then steps 805 through 821 are executed in this embodiment.

In step 805, the service administrator 15 at server 400 loads client information into sever 400.

In step 807, the UUIDs are stored in the beacon(s).

In step 809, GPS coordinates are stored in the server 400 that correspond to estimated locations of the beacon(s).

In step 811, the MCD 100 searches for the client in server 400.

In step 815, the UUID of the beacon is then associated with the client.

In step 817, the MCD uses its internal GPS system to acquire GPS coordinates when near the beacon.

In step 819, client info, the UUID, GPS coordinates, and other information is uploaded to server 400.

In step 821, if the GPS coordinates of the beacon received by the server 400 differ from the estimated GPS coordinates previously stored in the server 400, the received GPS coordinates replace the previously stored GPS coordinates.

Processing then continues at step 919 forward, as originally described for FIGS. 9A and 9B.

Screenshots

The executable code 441 and prestored data 443 are run by controller 450 of server 400 to keep track of multiple clients, MSPs 3, tasks, status of tasks, schedules and other information.

Some of this information may be more clearly presented visually. Exemplary screen shots of the server 400 and MCD 100 are provided to illustrate at least one embodiment of the current invention.

Figure 10:
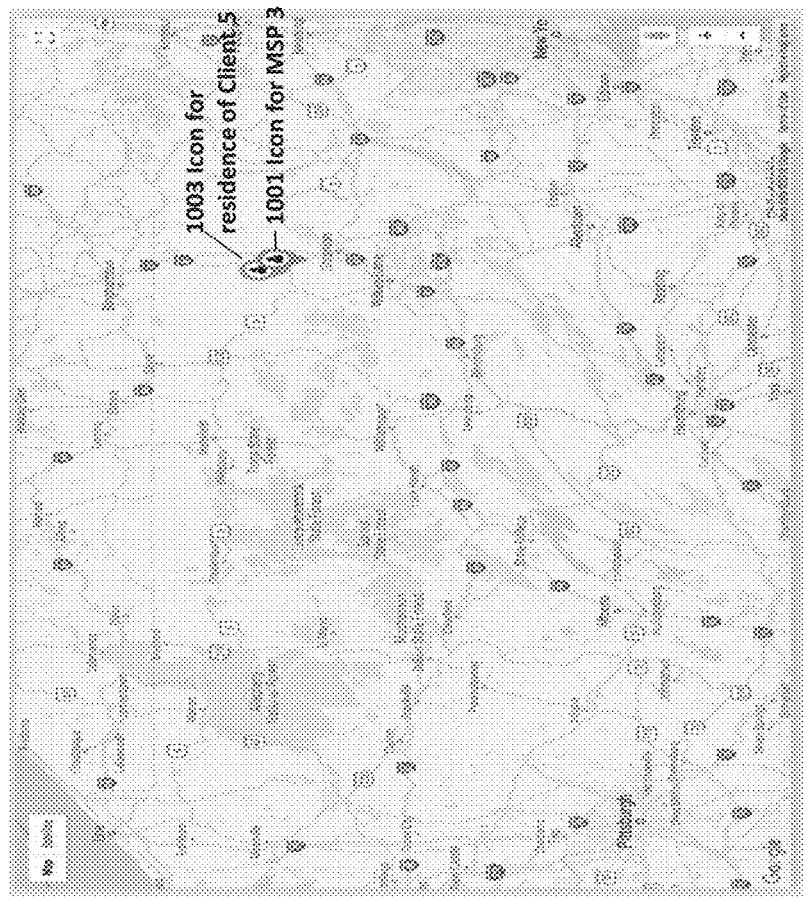
FIG. 10 show a current location of MSP as an icon on a map shows near a client's residence 7 shown as a second icon.

In FIG. 10, a current location of MSP 3 is shown as an icon 1001 on a map shows near a client's residence 7 shown as icon 1003. It can be color coded to indicate that green shows that the MCD 100 is connected to a beacon. Gray can represent that the MCD 100 is not connected to the beacon. It could be disconnected if it is too far away from the beacon, if the MSP 3 left the residence 7, or if using a cell phone, it could be that the cell phone simply the phone fell asleep.

Figure 11:
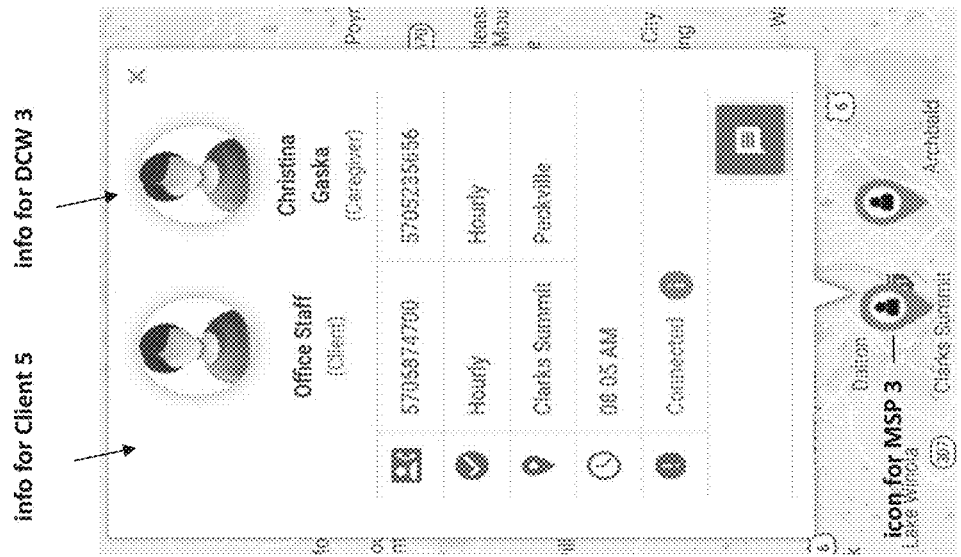
FIG. 11 illustrates information about the client and the MSP.

By clicking on either icon 1001, 1003 of FIG. 10, information is provided about the client 5 on the left and the MSP 3 on the right in FIG. 11. The blue button at the bottom may be used to send "push-type" messages to be sent from server 400 to MCD 100 of MSP 3.

Figure 12:
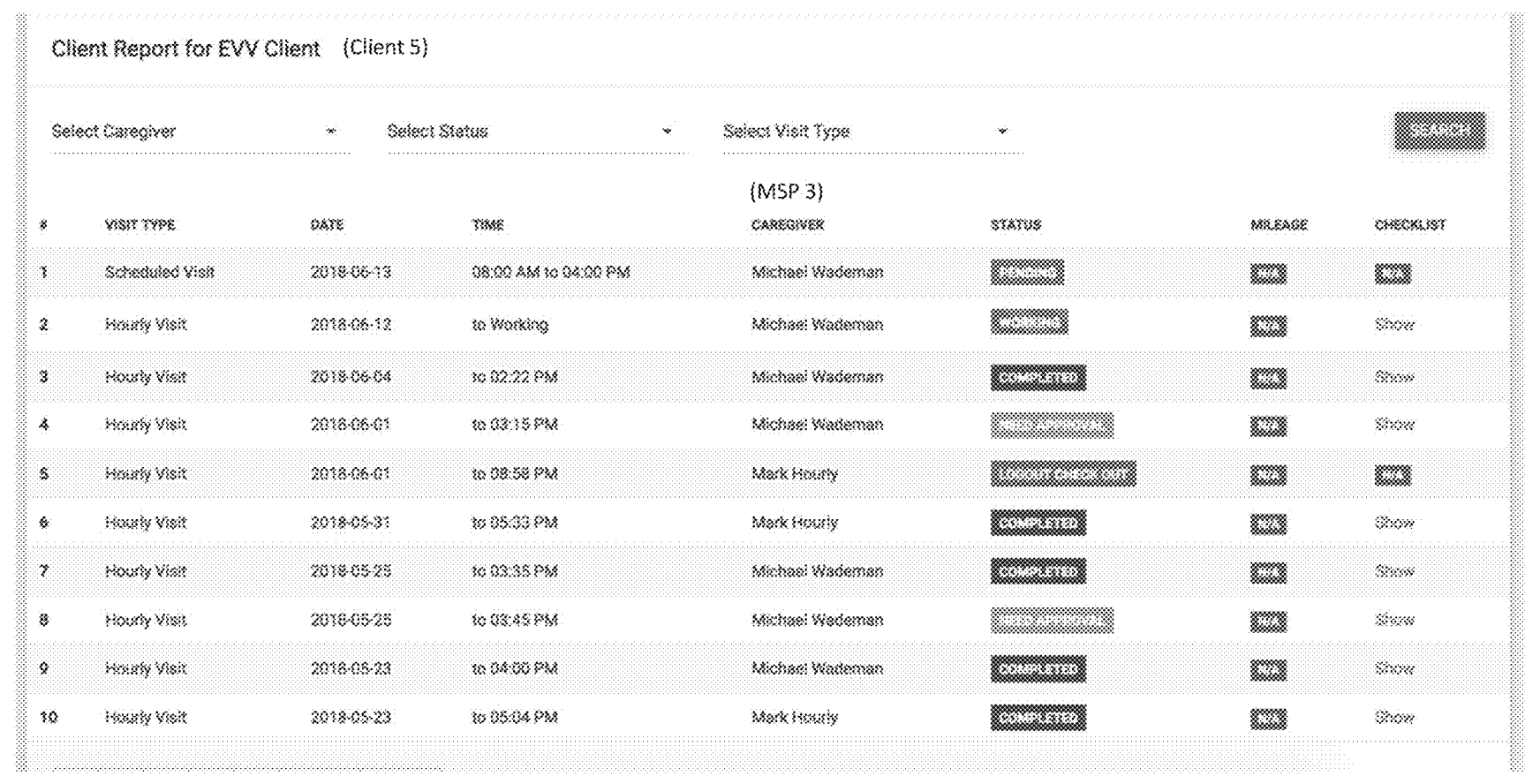

FIG. 12 shows a report for a client 5 indicating the MSPs 3 which visited client 5, the date/time and status of each visit.

Therefore, the visitor verification system 1000 described above in several different embodiments, can automatically authenticate a MSP 3, verify the time and location of a MSP session, periodically track the distance of the MSP 3 from a beacon (or track the location of the MSP 3 within the residence 7), acquire information where tasks were performed, and log the MSP 3 out of the system to end the session.

Figure 13:
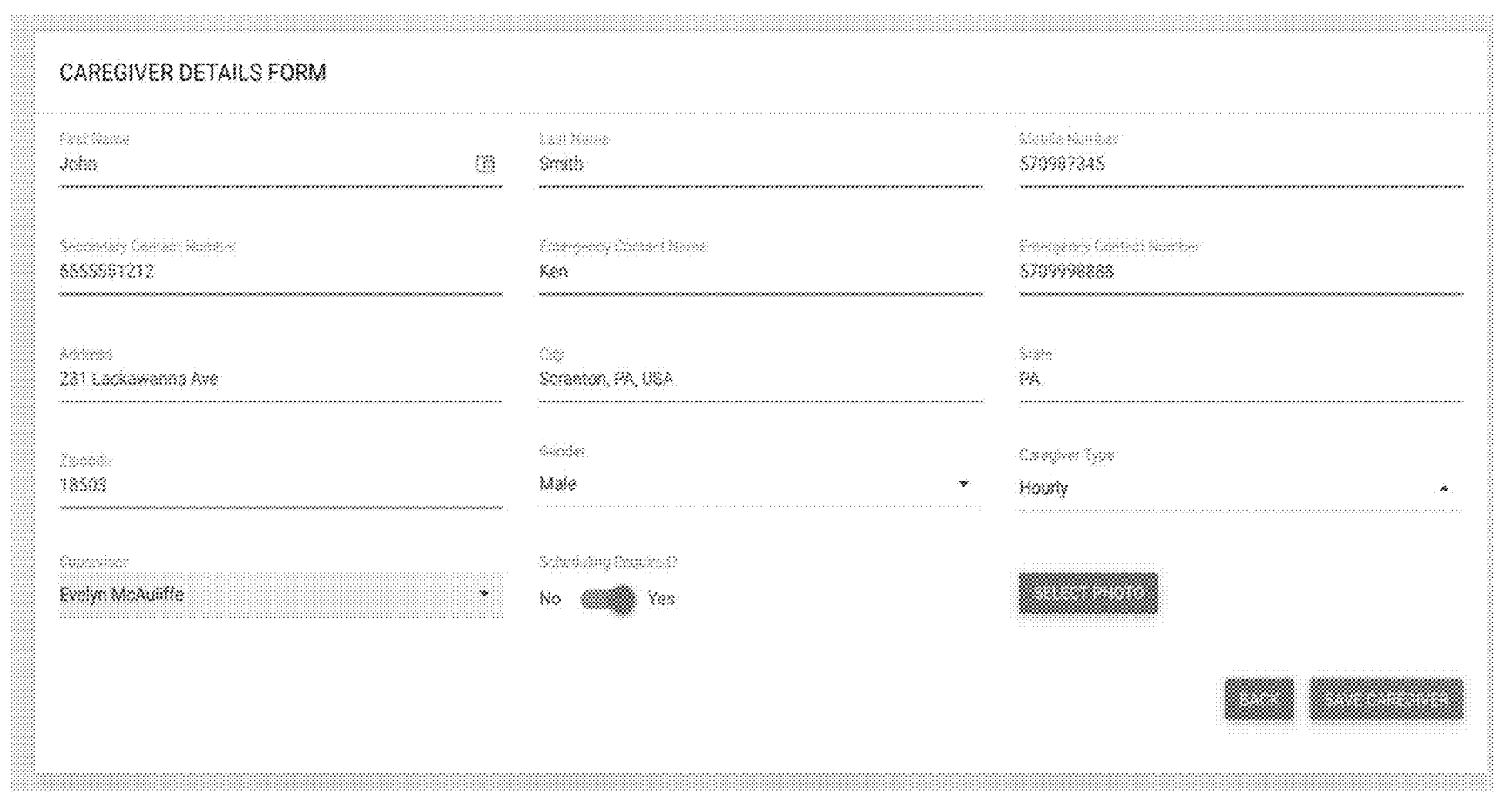

FIG. 13 shows typical information acquired for a MSP (caregiver), which may be displayed as shown.

Figure 14:
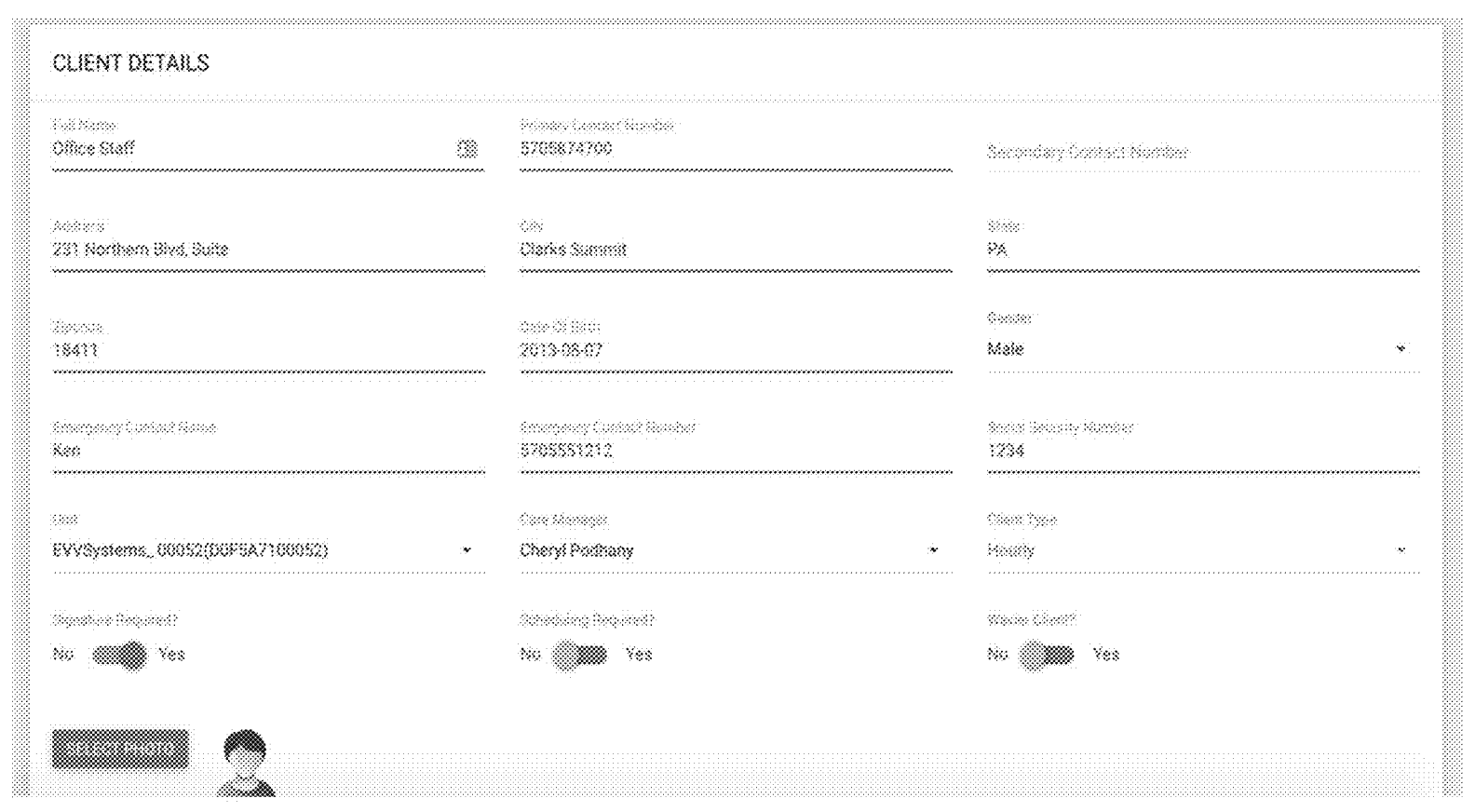

FIG. 14 shows typical information acquired for a client (patient) 5, which may be displayed as shown.

Figure 15:
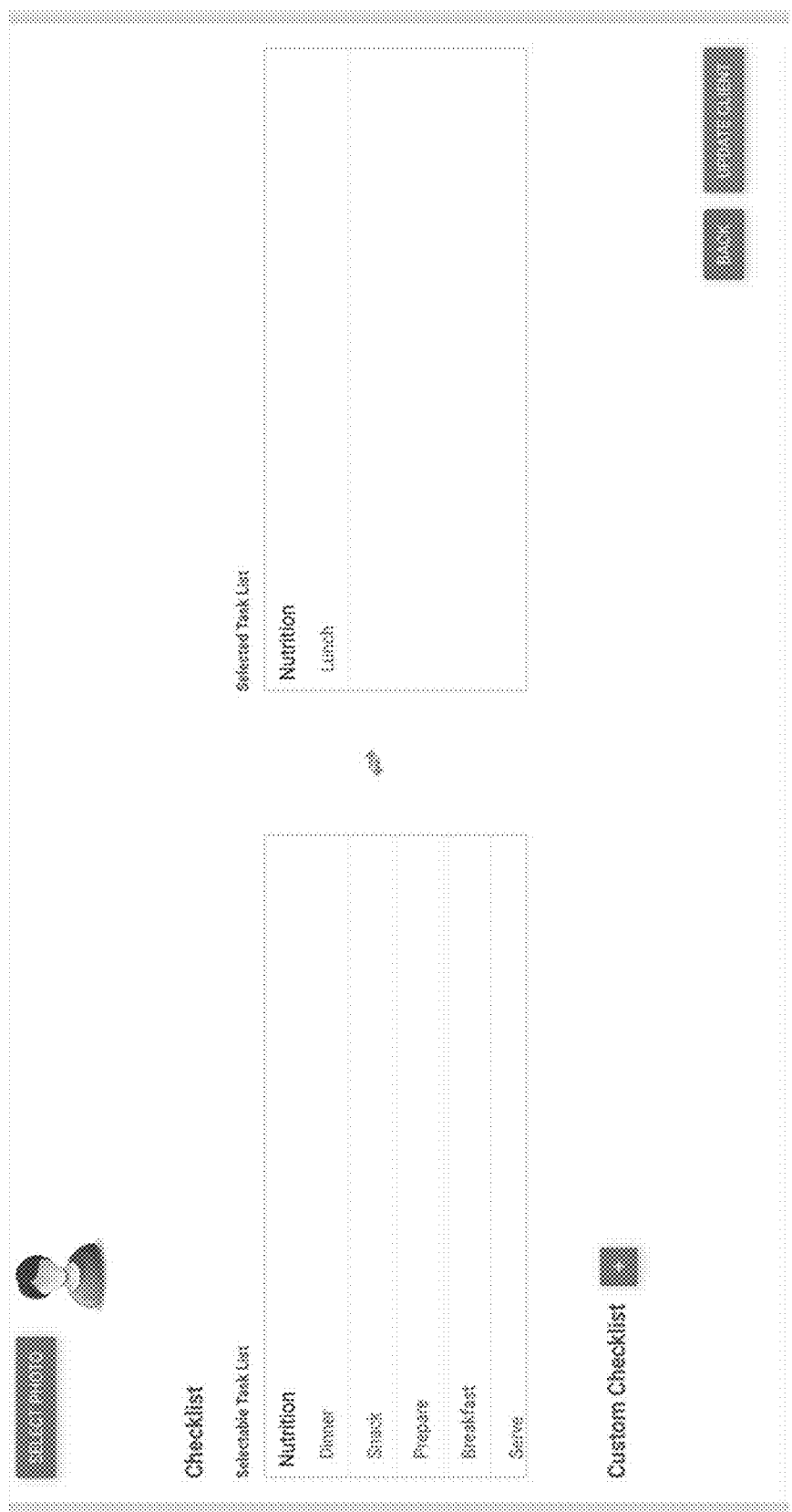
FIG. 15 is an exemplary screen shot illustrating used in setting up tasks in a schedule.

FIG. 15 shows a screen which allows a user, which may be a service administrator 15 to view and interact with I/O device 401 of server 400 to set up tasks. These tasks will be provided to the MCD 100 in a schedule. This schedule will be provided to the MCD 100 of the MSP 3 to be used for a client-specific care plan.

After the MCD 100 has been loaded by the server 400 with the proper information, such as the schedule and of tasks the MSP 3 has to perform on the client 5, the system changes from set-up mode to operational mode.

The MSP 3 starts the App which is executable code 141 stored in memory 140 of FIG. 4, shows a screen similar to that of FIG. 16.

Figure 18:
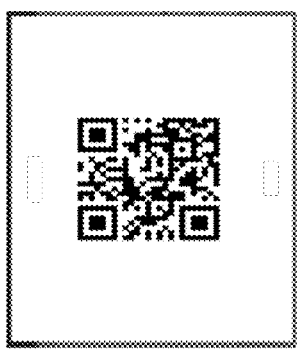
FIG. 18 is an example of a visual code which is a QR code.

Once logged in, a screen similar to that of FIG. 17 is shown. There is a scan button shown on the screen. Touching this button causes the MCD 100 to scan an optical pattern, such as the QR code shown in in FIG. 18, decode it and send it to server 400 for verification. If verified, then the MCD 100 is allowed access to the system.

Figure 19:
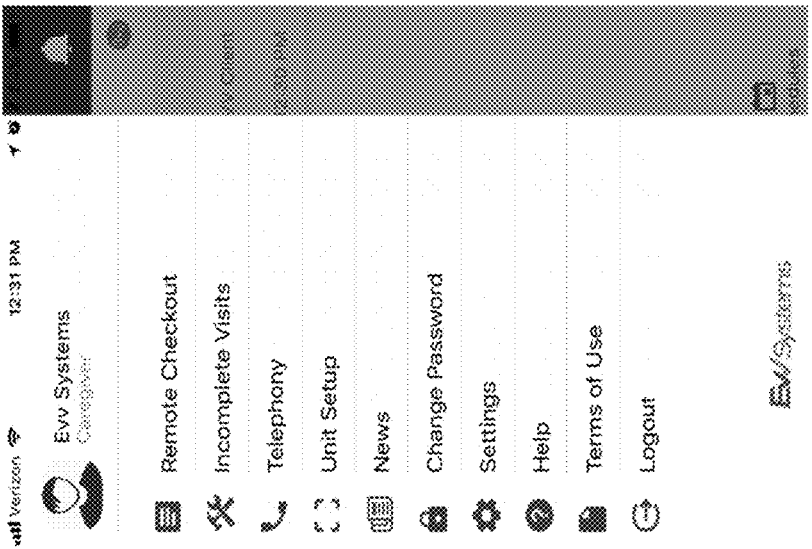
FIG. 19 is one of the main screens of the App running on the MCD.
Figure 20:
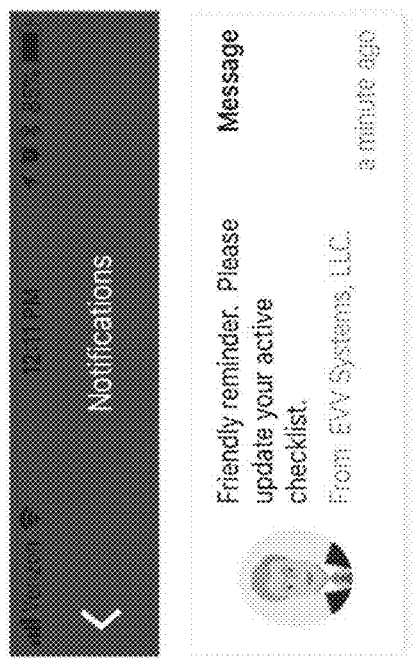
FIG. 20 show a notification on the MCD.

Once authenticated, the MSP may be able to access a screen similar to FIG. 19. There also may be displayed a notification, such as the one shown in FIG. 20, if there are tasks not yet in the checklist for this MSP 3.

Figure 21:
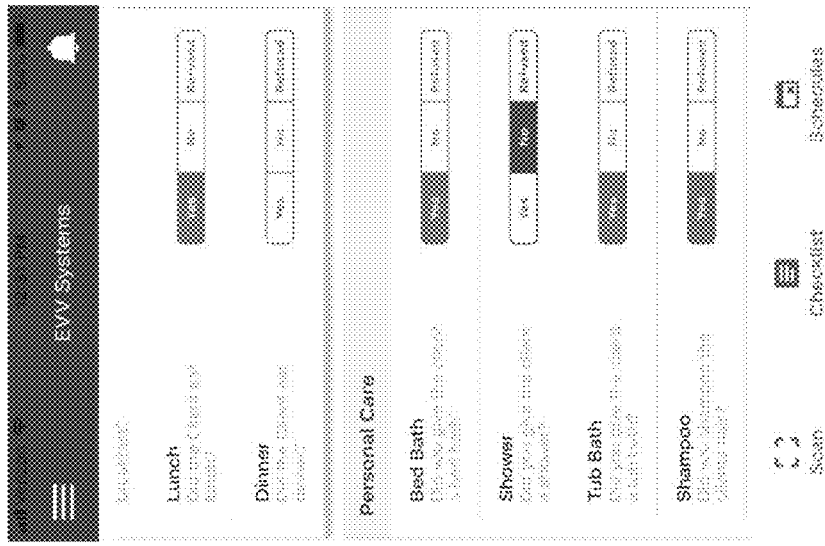
FIG. 21 shows the task update screen allowing the MSP to update the status of various tasks.
Figure 22:
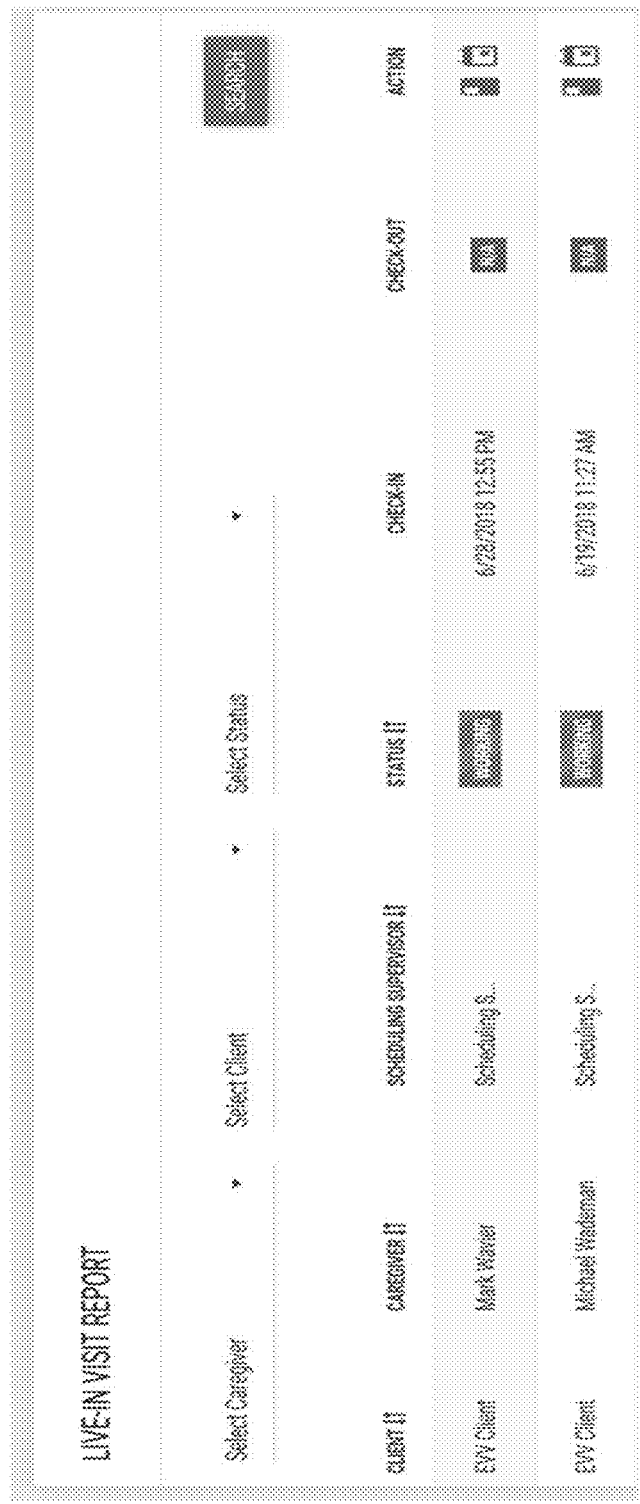
FIG. 22 show a screen of the server 400 that indicates the current status of the tasks as they are interactively updated.

MSP 3 than may select "Incomplete Visits" (or similar button) on the MCD 100 screen 110 which displays the image shown in FIG. 21. MSP 3 then updates the completed tasks or begins performing tasks yet to be completed. These tasks can be set to an "working", or similar status, as shown in FIG. 22.

Since the MCD 100 can be tracked, a report, such as that shown in FIG. 23 can be displayed showing the locations over time for one or more MCDs 100. Please note that an alternative embodiment, longitude and latitude are not tracked. In other embodiments, tracking is only active when the MSP 3 is logged in for work.

Figure 24:
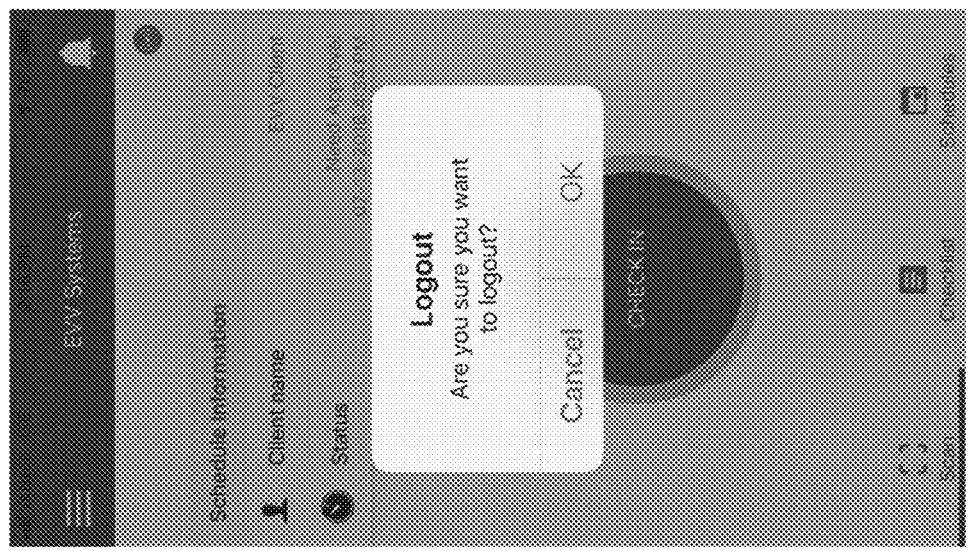
FIG. 24 shows a log-out screen which is compatible with the current invention.

FIG. 24 shows a log-out screen which is compatible with the current invention.

The current Employee Visit Verification System is a non-invasive system which is simple to use and requires minimal changes to the residence 7 of the client 5 in which it will be used. It is accurate and flags possible fraud, and does not require cameras or microphone which give the MSP 3 or the client 5 the impression that their privacy rights are being compromised.

While the present disclosure illustrates various aspects of the present teachings, and while these aspects have been described in some detail, it is not the intention of the applicant to restrict or in any way limit the scope of the claimed systems and methods to such detail. Additional advantages and modifications will readily appear to those skilled in the art. Therefore, the teachings of the present application, in its broader aspects, are not limited to the specific details and illustrative examples shown and described. Accordingly, departures may be made from such details without departing from the spirit or scope of the teachings of the present application. Moreover, the foregoing aspects are illustrative, and no single feature or element essential to all possible combinations may be claimed in this or a later application.

We claim:

1. A visit verification (VV) system for verifying visits by a Mobile Service Provider (MSP) to a residence of a client comprising:
   a. a beacon having:
      i. a transmitter configured for transmitting a signal;
      ii. a visual code;

b. a mobile computing device (MCD) having:
   i. an optical device configured for reading the visual code on the beacon;
   ii. a receiver capable of receiving the signal from the beacon,
   iii. a controller configured for determining the distance from the beacon based upon the received signal;
   iv. a communication device configured for communicating information from the MCD;
c. a server comprising:
   i. a network adapter configured for receiving information from the MCD,
   ii. a memory configured for storing information;
   iii. an input/output (I/O) device configured for providing output to, and receiving input from a user;
   iv. a controller connected to the network adapter, the memory, the I/O device, configured to:
   1. authenticate an MSP;
   2. determine when the MSP is outside of an acceptable perimeter:
   3. store task status information from the MCD.

2. The VV system of claim 1, further comprising an Interactive voice response (IVR) server having a voice recognition device allowing the MSP to speak over a telephone line to authenticate the MSP.

3. The VV system of claim 1, wherein the visual code is a QR code printed on a sticker.

4. The VV system of claim 1, wherein the visual code is a changeable image displayed on an electronic screen.

5. The VV system of claim 1, wherein the communication device is at least one of: a cellular device configured for communicating on a cellular network, a Bluetooth device configured for communicating with other Bluetooth devices, and a Wi-Fi device configured for communicating with other Wi-Fi devices.

6. The VV system of claim 1 wherein the information communicated by the communication device of the MCD is at least one of: the visual code, login information, RSSI, distance from beacon, longitude, latitude, tasks completed, and task status.

7. The VV system of claim 1, wherein the information communicated by the communication device of the MCD is at least one of: RSSI, distance from beacon, longitude, latitude, task status information.

8. The VV system of claim 1, wherein the controller of server runs executable code in memory configured to:
   a. receive the visual code from the optical device of the MCD;
   b. verify the visual code received corresponds to a proper code stored in prestored data;
   c. monitor the distance of the MCD from the beacon;
   d. determine when the distance between the MCD and the beacon is greater than a predetermined maximum;
   e. provide a schedule of tasks to the MCD;
   f. receive information as to the status of tasks from the MCD.

9. The VV system of claim 8, wherein the controller of server runs executable code that displays information of a plurality of MSPs that visited a given client in a defined time period.

10. The VV system of claim 1, wherein the MCD is a cell phone.

11. The VV system of claim 1, wherein server runs executable code that:
   a. provides MCD with a schedule of tasks that MSP is to assist client at specific locations;
   b. receives the status of tasks being performed from MCD;
   c. notifies MCD of tasks not yet completed; and
   d. receives details of time and location of task completion from MCD.

12. The VV system of claim 2, wherein server can interactively acquire and display status of tasks for a plurality of MSPs.

13. The VV system of claim 1, wherein a computing device flags tasks that have been reported to be performed, but do not correspond to a distance from the beacon that the tasks are typically completed.

14. The VV system of claim 13, wherein the computing device is one of the MCD, and the server.

15. The visit verification (VV) system of claim 10, wherein the information the controller of server provides to MCD is a schedule indicating clients to visit at specific dates/times, and locations of the clients' residences.

16. The visit verification (VV) system of claim 10, wherein the information the controller of MCD provides to server is current location, distance from beacon, and status of task to complete.

* * * * *